(12) United States Patent  (10) Patent No.: US 12,404,783 B2
Porro et al.  (45) Date of Patent: Sep. 2, 2025

(54) METHOD AND SYSTEM FOR OPERATING A GAS COMPRESSOR IN AN AMMONIA AND UREA PLANT

(71) Applicant: Yara International ASA, Oslo (NO)

(72) Inventors: Lino Giovanni Porro, Etterbeek (BE); Pieter Vidts, Gentbrugge (BE); Nils D'Hoker, Gentbrugge (BE)

(73) Assignee: YARA INTERNATIONAL ASA, Oslo (NO)

( * ) Notice: Subject to any disclaimer, the term of this patent is extended or adjusted under 35 U.S.C. 154(b) by 102 days.

(21) Appl. No.: 17/926,334

(22) PCT Filed: May 26, 2021

(86) PCT No.: PCT/EP2021/063975
§ 371 (c)(1),
(2) Date: Nov. 18, 2022

(87) PCT Pub. No.: WO2021/239775
PCT Pub. Date: Dec. 2, 2021

(65) Prior Publication Data
US 2023/0193908 A1 Jun. 22, 2023

(30) Foreign Application Priority Data
May 26, 2020 (EP) .................................. 20176605

(51) Int. Cl.
*F01K 13/00* (2006.01)
*C01C 1/04* (2006.01)
(Continued)

(52) U.S. Cl.
CPC ............ *F01K 13/00* (2013.01); *C01C 1/0488* (2013.01); *C07C 273/04* (2013.01); *F04D 25/04* (2013.01); *F04D 25/06* (2013.01)

(58) Field of Classification Search
None
See application file for complete search history.

(56) References Cited

U.S. PATENT DOCUMENTS 6,786,059 B1 * 9/2004 Piao ..................... F25B 27/00
62/434
2011/0000180 A1 * 1/2011 Yoshinari ................. F02C 3/04
60/39.3
(Continued)

FOREIGN PATENT DOCUMENTS

CN 104829494 B 8/2016
CN 106988813 A * 7/2017 ............. F01K 27/02
(Continued)

OTHER PUBLICATIONS

Extended European Search Report issued in App. No. EP20176605, dated Oct. 26, 2020, 7 pages.
International Search Report and Written Opinion issued in App. No. PCT/EP2021/063975, mailing date Aug. 13, 2021, 12 pages.
Written Opinion issued in App. No. PCT/EP2021/063975, mailing date Apr. 8, 2021, 5 pages.
(Continued)

*Primary Examiner* — Laert Dounis
(74) *Attorney, Agent, or Firm* — DILWORTH IP, LLC

(57) ABSTRACT

The present disclosure provides a plant comprising an ammonia-producing unit and a urea-producing unit. The urea-producing unit comprises a gas compressor, a steam turbine fluidly connected to the ammonia-producing unit for receiving steam produced by the ammonia-producing unit, and connected to the gas compressor for providing power to the gas compressor, and an electric motor, wherein the electric motor is connected to the gas compressor and configured to provide power to the gas compressor. The present disclosure also provides a method for operating an ammonia and urea plant, and a method to revamp an ammonia and urea plant.

14 Claims, 1 Drawing Sheet

(51) Int. Cl.
    *C07C 273/04*    (2006.01)
    *F04D 25/04*     (2006.01)
    *F04D 25/06*     (2006.01)

(56) References Cited

U.S. PATENT DOCUMENTS

| | | |
|---|---|---|
| 2014/0364647 A1 | 12/2014 | Iaquaniello |
| 2017/0283371 A1 | 10/2017 | Skinner |
| 2018/0222752 A1* | 8/2018 | Merritt, Jr. ................ C01B 3/48 |
| 2020/0071167 A1* | 3/2020 | Cerea ...................... C01B 21/28 |
| 2021/0261425 A1* | 8/2021 | Rossi ..................... C01C 1/0494 |

FOREIGN PATENT DOCUMENTS

| | | | |
|---|---|---|---|
| CN | 113864002 A | * | 12/2021 |
| EP | 20176605 | | 5/2020 |
| JP | S61133404 A | * | 6/1986 |
| RU | 2440977 C1 | | 1/2012 |
| RU | 2682601 C2 | | 3/2019 |
| WO | 2015/193108 A1 | | 12/2015 |
| WO | 2018052304 A1 | | 3/2018 |
| WO | 2020104197 A1 | | 5/2020 |

OTHER PUBLICATIONS

International Preliminary Report on Patentability issued in App. No. PCT/EP2021/063975, mailing date Jun. 29, 2022, 14 pages.
Office Action received for Russian Patent Application No. 2022130277, mailed on Aug. 21, 2024, 8 pages of English translation only.
Notice of Opposition issued against European Patent No. 4158160, dated May 14, 2025.
Berry, Jim; "A Dual Drive"; reprinted from World Pipelines Oct. 2008; www.worldpipelines.com.
UREA; Ullmann's Encyclopedia of Industrial Chemistry; vol. 37; pp. 657-695.
G.B. Marin, ed. (2011) Advances in Chemical Engineering, Multiscale Simulation and Design, vol. 40, p. 148-149.
Sandberg, Mark R.; "Centrifugal Compressor Configuration", 45th Turbomachinery & 32nd Pump symposia, Houston, Texas, Sep. 12-15, 2016.
Brown, Compressor: Selection and Sizing, 2011 (approximately 500 pages; selected pages from Google Books).
Dooyeweerd, E. et al.; "How the Cost Relation of Power and Steam Can Affect Urea Plant Design"; AIChE 1983 Summer National Meeting, Denver, Colorado; pp. 451-457.

\* cited by examiner

METHOD AND SYSTEM FOR OPERATING A GAS COMPRESSOR IN AN AMMONIA AND UREA PLANT

FIELD OF THE INVENTION

The present disclosure is related to the field of urea production. In particular, it is related to a plant comprising an ammonia-producing unit and a urea-producing unit comprising a gas compressor, a steam turbine and an electric motor. Further, the present disclosure provides a method for operating the gas compressor in an ammonia and urea plant.

BACKGROUND OF THE INVENTION

Urea is one of the most important chemicals industrially produced today, around 200 million tons of urea is produced worldwide every year. Most of it (above 90% of total production) is used as a fertilizer in agriculture as a nitrogen source. Urea is produced by reacting ammonia ($NH_3$) and carbon dioxide ($CO_2$) in a two-step process: first, two molecules of ammonia react with one molecule of carbon dioxide to form ammonium carbamate ($H_2N$—$COONH_4$); secondly, ammonium carbamate decomposes into urea and water.

In the first step of the process, streams of gaseous $CO_2$ and ammonia are mixed in a synthesis reactor. The reaction is carried out at high pressure (above 100 bar) to drive the reaction and increase production rates. The stream of $CO_2$ needs to be compressed under similar pressures before being injected in the synthesis reactor: this step is performed by gas compressors, i.e. a $CO_2$ compressor.

A gas compressor requires a great amount of energy to operate and this energy can be supplied by a variety of devices such as turbines and motors.

A plant comprising a urea-producing unit often also comprises an ammonia-producing unit, since the synthesis of urea requires ammonia. An ammonia-producing unit is a net exporter of steam, meaning that it produces more steam than it consumes, and one way to use that steam is to install steam turbines to power the $CO_2$ compressor of the urea-producing unit and to direct the steam from the ammonia-producing unit to the steam turbine to save cost for the plant.

However, the ammonia-producing unit usually does not produce enough steam to fully power the $CO_2$ compressor. The remaining steam required by the compressor may be obtained in different ways, but is often produced by burning a combustible, such as natural gas and coal, and boiling water with the energy released by the combustion in a so-called gas fired boiler. The number of boilers is depending by the complexity and required flexibility of the site.

Today, the environmental footprint of industrial production sites is under scrutiny because of the impact of using non-renewable and polluting energy sources, so there is a need to reduce the natural gas consumption in a plant comprising an ammonia-producing and a urea-producing unit.

In this disclosure, an ammonia and urea plant refers to a plant comprising one ammonia-producing unit and one urea-producing unit.

SUMMARY OF THE INVENTION

It was discovered that it was possible to replace one or more natural gas boilers, or at least reduce the natural gas consumption of the natural gas boilers, used to generate steam for the steam turbine connected to a gas compressor, for example the carbon dioxide compressor by one or more electric motors.

In a first aspect, the present disclosure provides a plant comprising an ammonia-producing unit and a urea-producing unit, comprising a gas compressor, a steam turbine fluidly connected to the ammonia-producing unit for receiving steam produced by the ammonia-producing unit, the steam turbine being also connected to the gas compressor, and configured to provide power to the gas compressor during operation of the urea-producing unit, and an electric motor, wherein the electric motor is connected to the gas compressor and configured to provide power to the gas compressor during operation of the urea-producing unit.

In another aspect, the present disclosure provides a method for operating a gas compressor in a plant according to the present disclosure, particularly during operation of the plant, comprising the step of providing power from the electric motor to the gas compressor, particularly simultaneously with providing power from the steam turbine to the gas compressor.

In another aspect, the present invention provides a method for decreasing the steam consumption of a urea-producing unit comprising a gas compressor connected to a steam turbine and configured to receive power from the steam turbine, comprising the steps of installing an electric motor; connecting the electric motor to the gas compressor; providing power from the electric motor to the gas compressor during operation of the urea-producing unit; and simultaneously providing power from the steam turbine to the gas compressor.

DETAILED DESCRIPTION OF THE INVENTION

Figure 1:
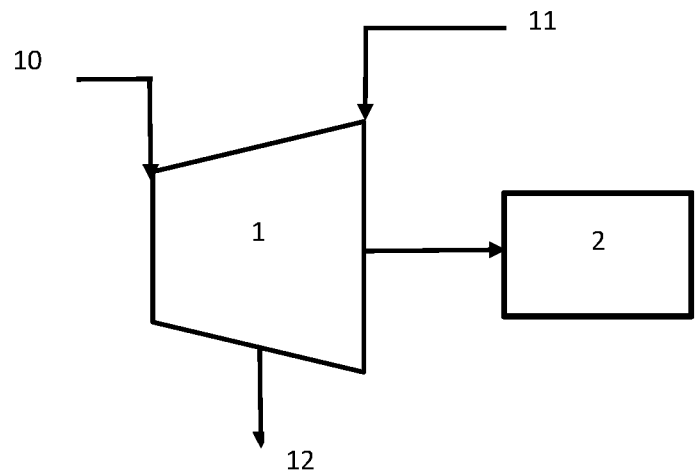
FIG. 1 represents a system comprising a steam turbine and a $CO_2$ gas compressor according to the prior art.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

All references cited in this description are hereby deemed to be incorporated in their entirety by way of reference.

As used herein, the following terms have the following meanings:

"A", "an", and "the" as used herein refers to both singular and plural referents unless the context clearly dictates otherwise. By way of example, "a unit" refers to one or more than one unit.

"About" as used herein referring to a measurable value such as a parameter, an amount, a temporal duration, and the like, is meant to encompass variations of +/−20% or less, in particular +/−10% or less, more in particular +/−5% or less, even more in particular +/−1% or less, and still more in particular +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "weight percent", "% wt" or "weight %", here and throughout the description unless otherwise defined, refers to the relative weight of the respective component based on the overall weight of the formulation.

The present application discloses a plant comprising an ammonia-producing unit and a urea-producing unit, comprising a gas compressor, a steam turbine fluidly connected to the ammonia-producing unit for receiving steam produced by the ammonia-producing unit, and connected to the gas compressor for providing power to the gas compressor, and an electric motor, wherein the electric motor is connected to the gas compressor and configured to provide power to the gas compressor.

In a first aspect, the present disclosure provides a plant comprising an ammonia-producing unit and a urea-producing unit, comprising a gas compressor, a steam turbine fluidly connected to the ammonia-producing unit for receiving steam produced by the ammonia-producing unit, the steam turbine being also connected to the gas compressor, and configured to provide power to the gas compressor during operation of the urea-producing unit, and an electric motor, wherein the electric motor is connected to the gas compressor and configured to provide power to the gas compressor during operation of the urea-producing unit.

As used herein, the term "during operation" of a unit or plant, in particular of a urea-producing unit, refers to the continuous operation mode wherein the unit or plant produces a product, in particular urea. A production cycle of a unit or plant comprises a start-up phase, wherein the different processes are initiated, a continuous and essentially constant phase or operation mode, wherein processes operate at a given working load that is usually kept constant during a production cycle; and a shutdown phase, where processes are slowly and safely stopped.

The present invention describes a plant and a method wherein the steam consumption of the plant during the continuous operation mode, i.e. the second phase as explained above, is reduced.

Boilers consuming natural gas have long been used in ammonia and urea plants to provide steam required by the different processes in the plant. The production of ammonia requires hydrogen gas, which is often produced by steam reforming, a process where natural gas is transformed into hydrogen and carbon dioxide. So, an ammonia and urea plant require the installation to receive and store natural gas in large quantities and adding additional boilers to a plant is seen as a cost-efficient manner to generate additional steam. Ammonia and urea plants are often located in natural gas-producing sites to benefit from large supplies of natural gas at competitive prices and are able to use some of that gas to generate steam.

A urea-producing unit often comprises three steam networks operating at different pressures: a high pressure steam network containing steam between 100 and 120 bar, in particular 110 bar, a medium pressure steam network containing steam between 30 and 50 bar, in particular 40 bar, and a low pressure steam network containing steam between 1 and 5 bar.

In one embodiment, the steam turbine connected to the gas compressor is operating with 40 bar steam. The pressure and amount of steam received by the turbine determines the maximum power that the turbine can produce.

However, burning natural gas to generate steam also produces a large amount of $CO_2$, which is a natural product of the reaction. Carbon dioxide is of course a powerful greenhouse gas effect and there is a large consensus in the political, industrial and scientific circles to reduce $CO_2$ emissions.

Another source responsible for important emissions of $CO_2$ are thermal power stations. A large number of these power stations uses non-renewable heat sources such as natural gas and/or coal. This sector is also trying to reduce its greenhouse footprint and the installation of power stations based on renewable sources such as wind, sunshine and waterfalls, is accelerating worldwide. Thus, there is an opportunity to modify the profile of energy consumption of an ammonia and urea plant to reduce its $CO_2$ emissions.

It was discovered that it was possible to replace one or more natural gas boilers used to provide steam to the steam turbine connected to a gas compressor of the urea-producing unit, or at least reduce the natural gas consumption of the natural gas boilers, by installing an electric motor that will provide power to the gas compressor. The steam turbine receives less steam and delivers less power to the compressor, but this difference in power is compensated by the electric motor. The presence of an electric motor and a steam turbine connected simultaneously to a single machine, the $CO_2$ gas compressor, increases the complexity of the plant because the two power sources need to be constantly balanced to provide a stable power supply to the gas compressor. Therefore, such a configuration is usually not favored over a simpler configuration where the $CO_2$ gas compressor is supplied in power by a single (steam) turbine or a single (electric) motor. Furthermore, this configuration may also require more maintenance and space in the plant, which increases the cost of installation and of running the plant.

Both the electric motor and the steam turbine are simultaneously providing power to the gas compressor during operation of the urea-producing unit. The amount of power provided by the electric motor and the steam turbine may vary over the course of the production in the urea-producing unit depending on parameters such as steam available in the plant, electricity available in the plant, or the cost of electricity.

As mentioned above, it is interesting to have a steam turbine in the urea-producing unit to consume steam produced by other production units, such as an ammonia-producing unit. Furthermore, a urea plant also produces steam at lower pressure, for example 4 bar. This lower-pressure steam is used in the urea-producing unit or by other processes which require steam to operate, such as heat exchangers. The steam in excess can be introduced into the steam turbine to provide additional power.

Electric motors are a well-known class of equipment and can be used to provide power to gas compressors, such as a $CO_2$ compressor in a urea-producing unit. The electric motor may be supplied in electricity from the grid to which the plant is connected to, but it may also be supplied by power stations located within the plant. For example, it may be envisaged to install solar panels and/or wind turbines within the plant to provide the electric motor with electricity. It is well known that renewable energy sources are intermittent, so the electric motor is often connected to the local electricity grid to compensate the irregular electricity production from renewable sources.

An electric motor to supply power to a gas compressor is particularly beneficial in a country where a major share of the electricity is produced using non-$CO_2$ emitting sources. Renewable sources such as wind, sunshine and waterfalls are non-$CO_2$ emitting sources. Nuclear power plants are not based on a renewable source (uranium); however, they are not emitting $CO_2$. Even if the local power grid is supplied by power plants using non-renewable energy sources, the use of an electric motor may provide some $CO_2$ savings as large power plants are usually more efficient than small boilers installed in fertilizer plants, such as an ammonia and urea plant.

As used herein, an electric motor is a device that is able to convert electricity into mechanical power. Within the context of the present disclosure, the electric motor is connected to a shaft that transfers the power generated by the electric motor to the gas compressor. The electric motor described herein typically does not convert mechanical power back into electricity.

The electric motor may be sized depending on the power required by the compressor and the loss in power produced by the steam turbine resulting in removing the natural gas boilers or reducing the production rate of the boilers.

In one embodiment, the electric motor is configured to provide 20 to 80% of the power required by the gas compressor. In one embodiment, the electric motor is configured to provide 20 to 50% of the power required by the gas compressor. In one embodiment, the electric motor is configured to provide 50 to 80% of the power required by the gas compressor. In one embodiment, the electric motor is configured to provide 30 to 70% of the power required by the gas compressor. The power to be supplied by the electric motor depends on the amount of steam that should be saved. The more steam that needs to be removed from the plant consumption, the more power the electric motor needs to supply.

In one embodiment, the steam turbine only receives steam from an ammonia-producing unit. It may be that the ammonia-producing unit produces enough steam to be provided to the steam turbine and achieve the required power production by the turbine. In that case, no natural gas boilers are required to produce additional steam. It may also be that the plant comprises a plurality, i.e. more than one, ammonia-producing units and that the plurality of ammonia-producing units all provide steam to the steam turbine of the urea-producing units. When a plant comprises more than one ammonia-producing unit, there is a greater chance that natural boilers are not required to provide steam to the steam turbine of the urea-producing unit.

In one embodiment, the plant comprising an ammonia-producing unit and a urea-producing unit, further comprises another steam-producing unit. Fertilizer plants may comprise other production units, related or not to fertilizer production. These units may produce steam that is not consumed within the unit and may be directed to a steam turbine in the urea-producing unit.

In one embodiment, the plant comprising an ammonia-producing unit and a urea-producing unit, further comprises a nitric acid-producing unit. Nitric acid is another important chemical for the production of fertilizers. It is reacted with a base such as ammonia or phosphate rock to produce solid fertilizer compositions. The production of nitric acid requires ammonia, so a plant comprising an ammonia-producing unit may also comprise a nitric acid-producing unit to utilize the ammonia produced in the plant. A nitric acid-producing unit comprises a plurality of pieces of equipment such as reactors, heat exchangers and more. A nitric acid-producing unit is also a net exporter of steam, which may be provided to the steam turbine of a gas compressor of the urea-producing unit.

In one embodiment, the nitric acid-producing unit is providing steam to the steam turbine connected to a gas compressor of the ammonia and urea plant according to the present disclosure.

In one embodiment, the steam turbine only receives steam from an ammonia-producing unit and a nitric acid-producing unit.

In one embodiment, the gas compressor connected to the electric motor is a carbon dioxide compressor.

The present disclosure also discloses a method for operating a gas compressor in a plant according to the present disclosure, comprising the steps of: providing power from the electric motor to the gas compressor. The present disclosure also discloses a method for operating a gas compressor in a plant according to the present disclosure, particularly during continuous operation of the plant or urea production unit according to the present disclosure, comprising the steps of: providing power from the electric motor to the gas compressor, and simultaneously providing power from the steam turbine to the gas compressor.

It was discovered that it is an advantage to connect a gas compressor of a urea-producing unit to a steam turbine and an electric motor. The ammonia-producing unit, and optionally the nitric acid-producing unit, comprised in the plant provide steam to the steam turbine. Steam may also be produced in natural gas boilers.

The electric motor may be provided in electricity by local power stations, especially power stations based on renewable energies, and by the national electricity grid. The motor allows for the reduction in the natural gas consumption of the plant by providing power to the gas compressor. This method is particularly advantageous in countries where a major share of the electricity is produced using non-$CO_2$ emitting methods.

This aspect of the present disclosure may exhibit the same or similar features and technical effects as the first aspect, i.e. the plant according to the present disclosure, and vice versa.

During the continuous production of urea in the urea-producing unit, both the electric motor and the steam turbine continuously and simultaneously provide power to the gas compressor. The power provided by each unit may vary during a production run.

In another aspect, the present invention provides a method for decreasing the steam consumption of a urea-producing unit comprising a gas compressor connected to a steam turbine and configured to receive power from the steam turbine, comprising the steps of: installing an electric motor; connecting the electric motor to the gas compressor; providing power from the electric motor to the gas compressor during operations of the urea-producing unit; and simultaneously providing power from the steam turbine to the gas compressor.

An electric motor is installed and connected to the gas compressor. During operation of the urea-producing unit, the electric motor is supplied with electricity, that may be generated from renewable energies, such as hydroelectric, wind, solar and tidal, and provides mechanical power to the gas compressor. As a consequence, the existing steam turbine does not need to provide as much power to the gas compressor as in prior art systems, i.e. in the absence of the electric motor, so the amount of steam provided to the steam turbine can be decreased. In such urea-producing units, steam is usually produced by burning natural gas and heating water with the resulting heat. So decreasing the required amount of steam by the plant or the unit allows to reduce the amount of natural gas burnt to produce steam, and reduces the carbon dioxide emissions caused by the steam production.

The gas compressor may be a syngas compressor, a carbon dioxide compressor, or an ammonia compressor.

In one embodiment, the ammonia-producing unit supplies steam to the steam turbine of the urea-producing unit.

In one embodiment, the plant comprises a nitric acid-producing unit and the nitric acid-producing unit supplies steam to the steam turbine of the urea-producing unit.

In another aspect, the present disclosure provides a method for revamping a plant comprising an ammonia-producing and a urea-producing unit comprising a gas compressor and a steam turbine fluidly connected to the ammonia-producing unit for receiving steam produced by the ammonia-producing unit, connected to the gas compressor for providing power to the gas compressor, and a natural gas boiler connected to the steam turbine. The method comprises the steps of: installing an electric motor connected to the gas compressor and configured to provide power to the gas compressor; and optionally, disconnecting the natural gas boiler from the steam turbine.

This aspect of the present disclosure may exhibit the same or similar features and technical effects as the first aspect, i.e. the plant according to the present disclosure, and vice versa.

It is possible to adapt an existing ammonia and urea plant where the steam turbine for a gas compressor of the urea-producing unit is provided steam from one or more natural gas boilers. It is indeed possible and relatively easy to install an electric motor to provide power to a gas compressor. Motors are available in a wide range of design, size and performance, so it may be possible to find a suitable motor for most of the existing ammonia and urea plants. Once the motor is installed, the need for steam for the steam turbine is reduced. This reduction may lead to the situation where one or more natural gas boilers are no longer required to operate at all, and thus may be disconnected from the steam turbine. They may be re-assigned to another task within the plant or simply decommissioned. Alternatively, the reduction in steam required may only lead to a lower usage rate if the natural gas boilers. Instead of operating the boilers at 90% capacity, it may be possible to operate them at less than 80% capacity, in particular less than 70% capacity, thus prolonging their lifetime, and/or facilitating maintenance.

In one embodiment, the electric motor is installed and connected to a carbon dioxide compressor of the urea-producing unit.

Example 1

In a plant comprising an ammonia-producing unit, a urea-producing unit and a nitric acid-producing unit, the urea-producing unit comprises a steam turbine (1) to provide power to the $CO_2$ compressor (2).

FIG. 1 represents the initial system, i.e. the prior art: the steam turbine received 215 ton/hour (t/h) of 40 bar steam (stream (10)) and produces 19.7 MW of power for the $CO_2$ compressor. Of the 215 t/h, 145 t/h are produced in the ammonia-producing and the nitric acid-producing units, and 70 t/h are produced by natural gas boilers. Additionally, 18 t/h of 4 bar steam (stream (11)), produced in excess in the urea-producing unit, are injected into the steam turbine, while 138 t/h of 20 bar steam (stream (12)) are extracted from the steam turbine and used into the urea-producing unit.

Figure 2:
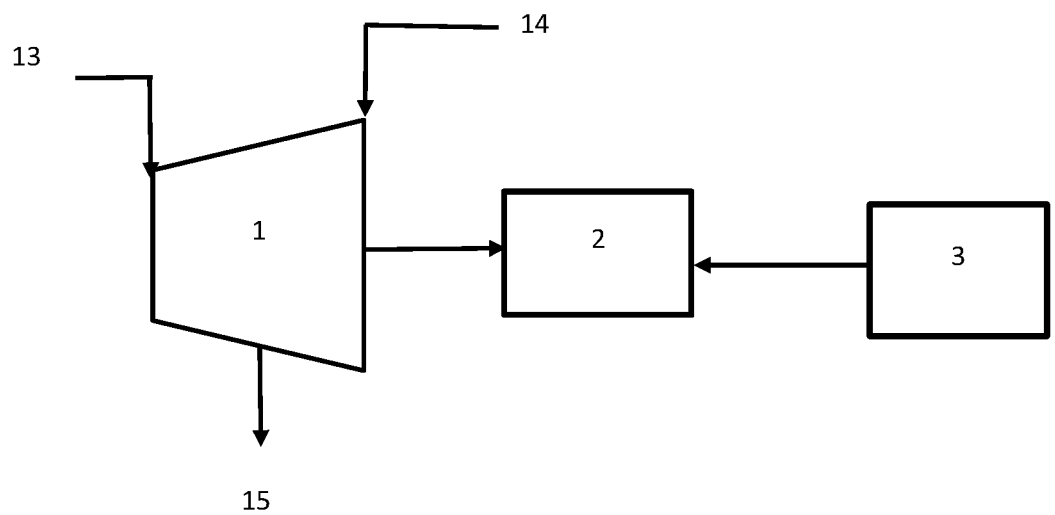
FIG. 2 represents a system comprising a steam turbine, a $CO_2$ gas compressor and an electric motor according to the present disclosure.

FIG. 2 represents a system according to the present disclosure. An electric motor (3) is installed and connected to the $CO_2$ compressor (2). The electric motor is configured to produce 10.2 MW of power and to supply this power to the $CO_2$ compressor (2). The steam turbine (1) only needs to produce 9.5 MW, so the steam supply is reduced to 175 t/h (stream (13), of which 145 t/h is still produced by the ammonia-producing and nitric acid-producing units. Now, only 30 t/h of 40 bar steam, instead of 70 t/h, are produced by the natural gas boilers, which is equivalent to 5.4 ton $CO_2$ equivalent saved per hour. The steam turbine still receives 18 t/h of 4 bar steam (stream (14)) and 138 t/h of 20 bar steam (stream 15) is extracted from the turbine.

The invention claimed is:

1. A method for producing urea in a plant comprising an ammonia-producing unit and a urea-producing unit, the urea-producing unit including a gas compressor, a steam turbine fluidly connected to the ammonia-producing unit, the steam turbine connected to the gas compressor, and an electric motor connected to the gas compressor, the method comprising a steps of:
   the steam turbine receiving steam produced by the ammonia-producing unit, wherein only the ammonia-producing unit supplies steam to the steam turbine of the urea-producing unit,
   providing power from the steam turbine to the gas compressor during continuous operation of the urea-producing unit, which is a continuous phase in a production cycle wherein the urea-producing unit produces urea and operates at a given working load;
   continuously providing the power from the electric motor to the gas compressor during the continuous operation of the urea-producing unit, while simultaneously providing the power from the steam turbine to the gas compressor.

2. The method according to claim 1, wherein the electric motor provides 20 to 80% of the power required by the gas compressor during the continuous operation of the urea-producing unit, and the steam turbine provides a remainder of the power required.

3. The method according to claim 1, wherein the plant comprises a nitric acid-producing unit including a reactor and a heat exchanger.

4. The method according to claim 1, wherein the gas compressor is a carbon dioxide compressor.

5. A method for decreasing steam consumption of a urea-producing unit comprising a gas compressor connected to a steam turbine and configured to receive power from the steam turbine, comprising steps of:
   installing an electric motor;
   connecting the electric motor to the gas compressor;
   continuously providing power from the electric motor to the gas compressor during continuous operation of the urea-producing unit, which is a continuous phase in a production cycle wherein the urea-producing unit produces urea and operates at a given working load; and
   simultaneously providing power from the steam turbine to the gas compressor, wherein the steam turbine receives steam only from an ammonia-producing unit and a nitric acid-producing unit including a reactor and a heat exchanger.

6. The method according to claim 5, wherein the electric motor provides 20 to 80% of the power required by the gas compressor during the continuous operation of the urea-producing unit and steam turbine provides a remainder of the power required.

7. The method according to claim 5, wherein the gas compressor is a carbon dioxide compressor.

8. The method according to claim 5, wherein the electric motor provides the power to the gas compressor via a shaft, wherein the electric motor does not convert mechanical power back into electricity.

9. The method according to claim 1, wherein the electric motor provides the power to the gas compressor via a shaft, wherein the electric motor does not convert mechanical power back into electricity.

10. A method for revamping a plant comprising an ammonia-producing and a urea-producing unit comprising a gas compressor and a steam turbine fluidly connected to the ammonia-producing unit for receiving steam produced by the ammonia-producing unit, connected to the gas compressor for providing power to the gas compressor, and a natural gas boiler connected to the steam turbine, the method comprising steps of:

installing an electric motor connected to the gas compressor, disconnecting the natural gas boiler from the steam turbine such that the steam turbine receives steam only from the ammonia-producing unit, providing power from the steam turbine to the gas compressor during continuous operation of the urea-producing unit, which is a continuous phase in a production cycle wherein the urea-producing unit produces urea and operates at a given working load; and continuously providing power from the electric motor to the gas compressor during continuous operation of the urea-producing unit while simultaneously providing power from the steam turbine to the gas compressor.

11. The method according to claim 10, wherein the electric motor provides 20 to 80% of the power required by the gas compressor during the continuous operation of the urea-producing unit and steam turbine provides a remainder of the power required.

12. The method according to claim 10, wherein the plant further comprises a nitric acid-producing unit including a reactor and a heat exchanger.

13. The method according to claim 10, wherein the gas compressor is a carbon dioxide compressor.

14. The method according to claim 10, wherein the electric motor provides the power to the gas compressor via a shaft, wherein the electric motor does not convert mechanical power back into electricity.

* * * * *